United States Patent
Perricone

(10) Patent No.: US 8,609,604 B2
(45) Date of Patent: *Dec. 17, 2013

(54) METHODS OF IMPROVING THE APPEARANCE OF AGING SKIN

(75) Inventor: Nicholas V. Perricone, Meriden, CT (US)

(73) Assignee: N.V. Perricone LLC, Meriden, CT (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/070,945

(22) Filed: Mar. 24, 2011

(65) Prior Publication Data

US 2011/0293743 A1 Dec. 1, 2011

Related U.S. Application Data

(63) Continuation-in-part of application No. 12/647,629, filed on Dec. 28, 2009, now abandoned.

(51) Int. Cl.
*A61K 8/64* (2006.01)
*A61K 38/06* (2006.01)

(52) U.S. Cl.
USPC .......................... 514/1.3; 514/18.8

(58) Field of Classification Search
None
See application file for complete search history.

(56) References Cited

U.S. PATENT DOCUMENTS

| | | | |
|---|---|---|---|
| 3,984,569 A | 10/1976 | Kalopissis et al. |
| 4,701,471 A | 10/1987 | Loucks, Sr. et al. |
| 4,784,685 A | 11/1988 | Meister |
| 5,376,361 A | 12/1994 | Perricone |
| 5,382,679 A | 1/1995 | Galzigna |
| 5,409,693 A | 4/1995 | Perricone |
| 5,464,825 A | 11/1995 | Anderson et al. |
| 5,472,698 A | 12/1995 | Rawlings et al. |
| 5,516,507 A | 5/1996 | N'Guyen et al. |
| 5,545,398 A | 8/1996 | Perricone |
| 5,554,647 A | 9/1996 | Perricone |
| 5,574,063 A | 11/1996 | Perricone |
| 5,624,955 A | 4/1997 | Nagasawa et al. |
| 5,643,586 A | 7/1997 | Perricone |
| 5,709,868 A | 1/1998 | Perricone |
| 5,874,444 A | 2/1999 | West |
| 5,879,690 A | 3/1999 | Perricone |
| 6,011,067 A | 1/2000 | Hersh |
| 6,030,948 A | 2/2000 | Mann |
| 6,191,121 B1 | 2/2001 | Perricone |
| 6,197,751 B1 | 3/2001 | Malinda et al. |
| 6,296,861 B1 | 10/2001 | Perricone |
| 6,437,004 B1 | 8/2002 | Perricone |
| 6,602,519 B1 | 8/2003 | Stevenson et al. |
| 6,627,732 B1 | 9/2003 | Sakon et al. |
| 6,821,524 B2 | 11/2004 | Marini |
| 6,979,459 B1 | 12/2005 | Perricone |
| 7,029,695 B2 | 4/2006 | Redelmeier et al. |
| 2004/0147452 A1 | 7/2004 | Yu et al. |
| 2005/0192229 A1 | 9/2005 | Perricone |
| 2005/0244359 A1 * | 11/2005 | Pelle et al. ................. 424/70.22 |
| 2006/0063718 A1 | 3/2006 | Perricone |
| 2006/0069036 A1 | 3/2006 | Perricone |
| 2006/0089310 A1 | 4/2006 | Goldstein et al. |
| 2006/0264360 A1 | 11/2006 | Girardi et al. |
| 2007/0015698 A1 | 1/2007 | Kleinman et al. |
| 2007/0093551 A1 | 4/2007 | Yu et al. |
| 2007/0160590 A1 | 7/2007 | McCleary |
| 2007/0207222 A1 | 9/2007 | Yu et al. |
| 2008/0050332 A1 | 2/2008 | Sivak |
| 2008/0051369 A1 | 2/2008 | Uemura et al. |
| 2009/0029944 A1 | 1/2009 | Skinner |

FOREIGN PATENT DOCUMENTS

| | | |
|---|---|---|
| CN | 1203073 A | 12/1998 |
| DE | 202005002324 U1 | 6/2006 |
| JP | 47-19775 B * | 6/1972 |
| JP | 49-35417 B * | 9/1974 |
| JP | 11263720 A | 9/1999 |
| JP | 2002047178 A | 2/2002 |
| WO | 0137788 A1 | 5/2001 |
| WO | 2004010968 A1 | 2/2004 |
| WO | 2009047728 A2 | 4/2009 |

OTHER PUBLICATIONS

Translation of JP 47-19775 B (Jun. 1972).*
Translation of JP 49-35417 B (Sep. 1974).*
Hawkins, et al.;"Clinical improvement to photoaged skin with conjugated linoleic acid (CLA): A novel cosmetic PPAR lipid for anti-aging benefits", Journal of the American Academy of Dermatology, C.V. Mosby, St. Louis, MO, US, vol. 56, No. 2, Feb. 1, 2007, p. AB95, XP005937048, ISSN: 0190-9622.
Bergamo Paolo et al: "Conjugated linoleic acid enhances glutathione synthesis and attenuates pathological signs in MRL/MpJ-Fas(lpr) mice", Journal of Lipid Research, vol. 47, No. 11, Nov. 2006, pp. 2382-2391, ISSN: 0022-2275.
Perluigi M., Joshi G, Sultana R., Calabrese V., De Marco C., Coccia R., Butterfield D.A. (2006); "In vivo protection by the xanthate tricyclodecan-9-ylxanthogenate against amyloid beta-peptide (1-42)-induced oxidative stress"; Neuroscience 138, 1161-1170 (abstract only).
International Search Report and Written Opinion of the International Searching Authority; PCT/US2010/055969; Dec. 27, 2010; 12 pages.
Pensalfini et al: "Protective effect of new S-acylglutathione derivatives against amyloid-induced oxidative stress", Free Radical Biology and Medicine, Elsevier Science, US, vol. 44, No. 8, Feb. 9, 2008, pp. 1624-1636, XP022575894.

* cited by examiner

*Primary Examiner* — Jeffrey E Russel
(74) *Attorney, Agent, or Firm* — St. Onge Steward Johnston & Reens LLC

(57) ABSTRACT

A method of preventing or treating conditions of peri-menopausal, menopausal, or post-menopausal skin comprising applying to the skin tissue, a safe and effective amount of a composition comprising between 1.0% to 3% by weight of S-palmitoyl glutathione and a dermatologically acceptable carrier.

83 Claims, No Drawings

METHODS OF IMPROVING THE APPEARANCE OF AGING SKIN

CROSS-REFERENCE TO RELATED APPLICATIONS

The present application is a continuation-in-part of U.S. patent application Ser. No. 12/647,629 entitled Topical Acyl Glutathione Formulations, filed Dec. 28, 2009 now abandoned, the content of which is incorporated herein by reference.

FIELD OF THE INVENTION

The present invention relates to use of formulations comprising acyl derivatives of glutathione to improve the appearance of aging skin and prevent and treat conditions of aging skin. More specifically, the present invention relates to use of topical compositions comprising S-palmitoyl glutathione to improve the appearance of wrinkles and fine lines, dryness, dullness or lack of radiance of skin, or to prevent or treat the appearance of exaggerated lines and wrinkles, sagging, discoloration, or redness and blotchiness of skin, all visible conditions of peri-menopausal, menopausal, or post-menopausal skin.

BACKGROUND OF THE INVENTION

Reduced glutathione, most commonly called glutathione or GSH, is a relatively small molecule found in animals and plants, having the following formula:

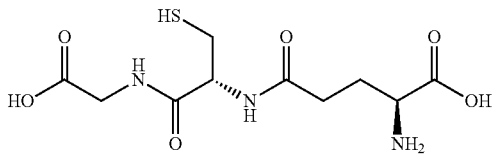 [SMILES: N[C@@H](CCC(=O)N[C@@H](CS)C(=O)NCC(=O)O)C(=O)O]

Glutathione is a water-phase orthomolecule. It is the smallest intracellular thiol molecule. It is a potent reducing compound due to its significant electron-donating capacity. Glutathione is a potent antioxidant and enzyme cofactor which plays a critical role in regulating cell activity.

Glutathione is a linear tripeptide of L-glutamine, L-cysteine, and glycine. Technically, N-L-gamma-glutamyl-cysteinyl glycine or L-glutathione, the molecule has a sulfhydryl (SH) group on the cysteinyl portion, which accounts for its strong electron-donating character. As electrons are lost, the molecule becomes oxidized, and two oxidized glutathione molecules become linked (dimerized) by a disulfide bridge to form glutathione disulfide or oxidized glutathione (GSSG). This linkage is reversible upon re-reduction. Glutathione is under tight homeostatic control both intracellularly and extracellularly. A dynamic balance is maintained between glutathione synthesis, its recycling from GSSG/oxidized glutathione, and its utilization.

Glutathione synthesis involves two closely linked, enzymatically controlled reactions that utilize ATP. First cysteine and glutamate are combined by gamma-glutamyl cysteinyl synthetase. Second, glutathione synthetase combines gamma-glutamylcysteine with glycine to generate glutathione. As glutathione levels rise, they self-limit further glutathione synthesis; otherwise, cysteine availability is usually rate-limiting. Fasting, protein-energy malnutrition, or other dietary amino acid deficiencies limit glutathione synthesis.

Glutathione recycling is catalyzed by glutathione disulfide reductase, which uses reducing equivalents from NADPH to reconvert GSSG to 2GSH. The reducing power of ascorbate helps conserve systemic glutathione. glutathione is used as a cofactor by (1) multiple peroxidase enzymes, to detoxify peroxides generated from oxygen radical attack on biological molecules; (2) transhydrogenases, to reduce oxidized centers on DNA, proteins, and other biomolecules; and (3) glutathione S-transferases (GST) to conjugate glutathione with endogenous substances (e.g., estrogens) and to exogenous electrophiles (e.g., arene oxides, unsaturated carbonyls, organic halides), and diverse xenobiotics.

Free radical and other oxidative agents can deplete glutathione. The homeostatic glutathione redox cycle attempts to maintain glutathione levels as it is being consumed. Amounts available from foods are limited (less than 150 mg/day), and oxidative depletion can outpace synthesis.

The liver is the largest glutathione reservoir. The parenchymal cells synthesize glutathione for P450 conjugation and numerous other metabolic requirements, then export glutathione as a systemic source of SH/reducing power. Glutathione is carried in the bile to the intestinal luminal compartment. Epithelial tissues of the kidney tubules, intestinal lining, and lung, have substantial P450 activity and modest capacity to export glutathione.

Glutathione equivalents circulate in the blood predominantly as cystine, the oxidized and more stable form of cysteine. Cells import cystine from the blood, reconvert it to cysteine (likely using ascorbate as cofactor), and from it synthesize glutathione. Conversely, inside the cell glutathione helps re-reduce oxidized forms of other antioxidants such as ascorbate and alpha-tocopherol.

Glutathione is an extremely important cell protectant. It directly quenches reactive hydroxyl free radicals, other oxygen-centered free radicals, and radical centers on DNA and other biomolecules. Glutathione protects skin, lens, cornea, and retina against radiation damage, and the biochemical foundation of P450 detoxication in the liver, kidneys, lungs, intestinal epithelia, and other organs.

Gluathione is the essential cofactor for many enzymes which require thiol-reducing equivalents, and helps keep redox-sensitive active sites on enzymes in the necessary reduced state. Higher-order thiol cell systems—the metallothioneins, thioredoxins, and other redox regulator proteins—are ultimately regulated by GSH levels and the GSH/GSSG redox ratio.

Glutathione and its metabolites also interface with energetics and neurotransmitter syntheses, through several prominent metabolic pathways. Glutathione availability downregulates the pro-inflammatory potential of leukotrienes and other eicosanoids.

Glutathione levels in human tissues normally range from 0.1 to 10 millimolar (mM), most concentrated in the liver (up to 10 mM) and in the spleen, kidney, lens, erythrocytes, and leukocytes. Plasma concentration is in the micromolar range (approx. 4.5 µM). Oxidative stressors that can deplete glutathione include ultraviolet and other radiation; viral infections; environmental toxins, household chemicals, and heavy metals; surgery, inflammation, burns, septic shock; and dietary deficiencies of glutathione precursors and enzyme cofactors.

A number of disclosures teach enhancing the cellular level of glutathione through administration of various glutathione derivatives. U.S. Pat. No. 5,464,825 (Anderson) discloses use of N-acyl monoalkyl glutathione monoester for increasing cellular levels in the liver and kidney cells to treat AIDS and other viral infections. U.S. Pat. No. 5,624,955 (Nagasawa) discloses glutathione prodrugs consisting of glutamyl cysteines derivatives to enhance glutathione level in the lens and prevent cataract onset. U.S. Pat. No. 7,029,695 (Redelmeier) discloses lipids formulations to enhance the bioavailability of analogs of glutathione for use in hematopoiesis modulation. Neuroscience 138:1161-1170 (2006) (Perlugig et al.) discloses use of Tricyclodecan-9-yl-xanthogenate to achieve an increase in glutathione levels in the neuronal cells to treat Alzheimer's disease. WO 2009/047728 (Liguri) discloses that lipophilic derivatives of glutathione may be useful in treating Alzheimer disease and Huntington chorea.

Topical uses of glutathione derivatives have been disclosed. U.S. Pat. No. 3,948,569 (Kalopissis) discloses use of S-substituted linear and branched alkyl and alkenyl derivatives of glutathione for various scalp and hair applications and to combat excessive sebum secretion. U.S. Pat. No. 5,516,507 (N'Guyen) discloses glutathione mono-alkyl esters for topical treatment of cutaneous aging. These glutathione mono-alkyl esters are substituted at the glycine residue and employ alkyl chains having only 1 to 10 carbons. U.S. Pat. App. 2004/0147452 (Yu) proposes the use of non-amphoteric N-acyl glutathione derivatives for topical application for a broad range of conditions. The non-amphoteric derivatives of glutathione are proposed due to the instability of aqueous pharmaceutical formulations of mono and diester prodrugs of glutathione, which rapidly deteriorate over time.

U.S. Pat. No. 6,011,067 (Hersh) discloses compositions comprising several synergistic antioxidants as adjuncts to topical therapy of desquamating inflammatory disorders, such as psoriasis, which compositions contain as active ingredients L-glutathione and a selenium compound. Hersh's disclosure stresses the importance of the presence of both ingredients to the anti-psoriatic effectiveness of the claimed composition.

My published applications, U.S. Patent Publications Nos. 20050192229, 20060063718, and 20060069036 disclose compositions with high glutathione concentrations for topical use in the treatment of psoriasis.

SUMMARY OF THE INVENTION

The present invention provides a method of improving the appearance of aging skin comprising applying to the skin tissue, a safe and effective amount of a composition containing S-acyl glutathione derivative of formula (I)

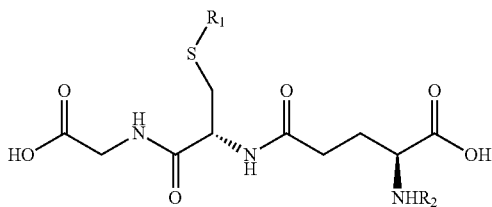

wherein $R_1$ consists of an unsaturated or saturated $C_{16}$ acyl group and $R_2$ is a hydrogen, aliphatic or aromatic acyl group; and a dermatologically acceptable carrier.

In preferred embodiments, $R_1$ is a palmitoyl group. In some of these embodiments, the composition comprises about 0.01% to 20% by weight of S-acyl glutathione derivative. In some of these embodiments, the composition comprises about 0.1% to 5% by weight of S-acyl glutathione derivative. In especially preferred embodiments, the composition comprises about 1.0% to 3% by weight of S-palmitoyl glutathione.

In some embodiments, the carrier comprises fatty acid derivatives of stearic acid.

In certain embodiments, the composition further comprises one or more additional ingredients selected from the group consisting of: ascorbic acid and ascorbic acid derivatives, lipoic acid, neuropeptides, α-hydroxy acids, salts of magnesium, zinc and copper, and tocotrienols and tocotrienol derivatives and vitamin E compositions enriched with tocotrienols or tocotrienol derivatives.

In some embodiments, the skin comprises lines and wrinkles, dryness, roughness, dullness or lack of radiance, or enlarged pores.

In certain preferred embodiments, the composition is applied to peri-menopausal, menopausal, or post-menopausal skin.

In another aspect, the invention provides a method of preventing or treating conditions of aging skin comprising applying to the skin tissue of a mammal in need of such regulation, a safe and effective amount of a composition containing S-acyl glutathione derivative of formula (I)

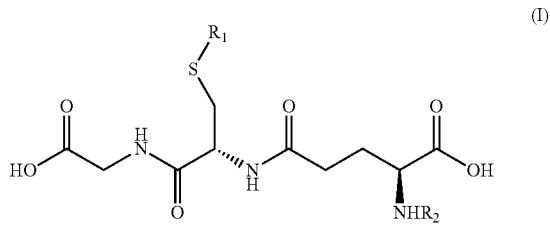

wherein $R_1$ consists of an unsaturated or saturated $C_{16}$ group and $R_2$ is a hydrogen, aliphatic or aromatic acyl group; and a dermatologically acceptable carrier.

In preferred embodiments, $R_1$ is a palmitoyl group. In some of these embodiments, the composition comprising about 0.01% to 20% by weight of S-acyl glutathione derivative. In certain of these embodiments, the composition comprises about 0.1% to 5% by weight of S-acyl glutathione derivative. In especially preferred embodiments, the composition comprises 1.0% to 3% by weight of S-palmitoyl glutathione.

In some embodiments, the carrier comprises fatty acid derivatives of stearic acid.

In certain embodiments, the composition further comprises one or more additional ingredients selected from the group consisting of: ascorbic acid and ascorbic acid derivatives, lipoic acid, neuropeptides, α-hydroxy acids, salts of magnesium, zinc and copper, and tocotrienols and tocotrienol derivatives and vitamin E compositions enriched with tocotrienols or tocotrienol derivatives.

In some embodiments, the skin condition comprises lines and wrinkles. In some of these embodiments, the lines and wrinkles comprise marionette lines. In other of these embodiments, the lines and wrinkles comprise eleven lines. In further of these embodiments, the lines and wrinkles comprise horizontal forehead lines.

In certain embodiments, the skin condition comprises sagging of skin. In other embodiments, the skin condition comprises severe dryness. In further embodiments, the skin condition comprises discoloration.

In some embodiments, the skin condition comprises redness or blotchiness. In some of these embodiments, the redness or blotchiness is comprised of spider vessels.

In especially preferred embodiments, peri-menopausal, menopausal, or post-menopausal skin is treated.

In yet another aspect, the invention provides a method of preventing or treating conditions of peri-menopausal, menopausal, or post-menopausal skin comprising applying to the skin tissue, a safe and effective amount of a composition comprising between 1.0% to 3% by weight of S-palmitoyl glutathione and a dermatologically acceptable carrier.

DETAILED DESCRIPTION OF THE INVENTION

Aging of skin cells often is associated with glycation of proteins in the cells of the skin, which causes a loss of skin elasticity and the breakdown of collagen. Glycated proteins display conditions such as inflammation, wrinkles, and brown spots or lipofuscin.

Aging of the skin is also caused by the loss of estrogen or decline in oestrogen associated with menopause. Oestrogen receptors are most abundant around the face, genital area and lower limbs. The present invention recognizes these processes and provides compositions and methods to minimize both prospective and existing aging conditions and skin conditions associated with loss of estrogen and oestrogen during menopause.

The term "skin" means the keratinous surfaces skin, hair and nails. The term "skin" when used herein is in the broad sense meaning the skin of the face, body, and neck as well as the lips.

The present invention comprises topical S-acyl glutathione (GSH) compositions to prevent skin aging and address skin conditions associated with menopause. The compositions help address severe skin dryness, dullness, loss of elasticity, lack of radiance, exaggerated lines and wrinkles, spider vessels or red blotchiness. Particularly, "marionette" lines, smile lines, deep nasolabial fold lines, crow's feet, fine lines/wrinkles, vertical lines between the eyebrows, horizontal forehead lines, sagging thin/frail skin, skin redness and dullness may be improved using compositions of the invention. These compositions may also be referred to using IUPAC nomenclature as S-alkanoyl glutathione compositions. The treatments consist of S-acyl glutathione derivatives of the formula:

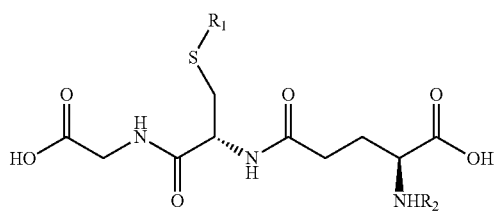

wherein $R_1$ is consists of a saturated or unsaturated aliphatic $C_{12}$-$C_{24}$ acyl group, preferably $C_{16}$-$C_{24}$ group, most preferably a saturated $C_{16}$ group; and $R_2$ is a hydrogen, aliphatic or aromatic acyl group, and most preferably a hydrogen group. In preferred embodiments, $R_1$ is selected from the group consisting of linoleoyl, oleoyl or palmitoyl groups, but is most preferably a palmitoyl group. A particularly preferred embodiment of the invention comprises S-palmitoyl glutathione.

A particular object of the present invention is to provide S-acyl glutathione compositions having acyl groups to enhance skin penetration and transdermal absorption to improve the condition of the skin. The presence of the hydrocarbon chain of the apolar acyl group bonded to the glutathione thiol group enables the compounds of the invention to be effective as a topical application that can easily pass through the lipid bilayer of the cell membranes of epidermal and dermal cells. S-acyl glutathiones have lipophilic structures that make them fat soluble and able to pass through cell membranes and be absorbed directly into cells.

While not wishing to be bound by any theory, it is believed that palmitoyl groups in particular enhance the hydrophobicity and contribute to membrane association, similar to S-Palmitoylation observed with proteins. The association of the fatty acid chain is reversible (because the bond between palmitic acid and glutathione is a thio-ester bond) allowing the compound to be absorbed by the cell membranes.

S-acyl glutathione compounds of the present invention may be purchased or prepared by various means known to those of skill in the art. For example, enzymatic transthioesterification can be achieved by reacting glutathione with an appropriate acyl ester of coenzyme A (CoA) followed by purification from the water phase by HPLC or by chemically reacting glutathione with the corresponding acyl halide. See WO 2009/047728, supra, incorporated herein by reference. Another synthesis may be carried out by reacting the halide of the corresponding carboxylic acid with a solution of L-glutathione in trifluoroacetic acid under vacuum, adding ethyl acetate, and collecting the precipitated salt. See e.g. U.S. Pat. No. 3,984,569, supra, which is hereby incorporated by reference.

Topical compositions containing S-acyl glutathiones according to the present invention are intended to be topically applied to and absorbed by the skin tissue. S-acyl glutathiones activate transketolase, increasing its activity by 300%, and prevent protein glycation and AGE formation. After treatment for the recommended period of time, it is expected that decreased inflammation, irritation, and erythema of the skin will be observed, along with an increased skin elasticity and suppleness. Particularly, "marionette" lines, smile lines, deep nasolabial fold lines, crow's feet, fine lines/wrinkles, vertical lines between the eyebrows, horizontal forehead lines, sagging thin/frail skin, skin redness and dullness are reduced. The present invention thus is expected to improve the appearance of skin, prevent and treat skin aging, dryness, dullness, loss of elasticity and lack of radiance. Particularly, treatments may be used to prevent or retard the appearance of spider vessels or red blotchiness associated with menopausal skin. In another embodiment, treatments may be used to prevent or treat exaggerated lines and wrinkles.

Only effective amounts of topical compositions containing S-acyl glutathione are needed to achieve the aforementioned benefits and prevent typical menopausal and aging effects on the skin. Generally, topical application to skin tissue is accomplished in association with a dermatologically acceptable carrier, and particularly one in which the S-acyl glutathione is soluble per se or is effectively solubilized (e.g., as an emulsion or microemulsion). Where employed, the carrier is inert in the sense of not bringing about a deactivation or oxidation of the glutathione derived active ingredient(s), and in the sense of not bringing about any adverse effect on the skin areas to which it is applied.

In one preferred practice of the invention, one or more S-acyl glutathione derivatives is applied in admixture with the dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the carrier for the topical composition can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent(s). Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters, or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. In the preferred embodiment, the carrier is an oil in water emulsion.

As noted, these ingredients can be formulated into a cream, lotion, or gel, or a solid stick, by utilization of different proportions of the ingredients and/or by inclusion of thickening agents such as gums or other forms of hydrophilic colloids. One possible embodiment is a solution used to saturate a pad used to wipe affected areas; another is a cleanser; and others are lotions, creams, and gels, which are referred to herein as dermally or dermatologically acceptable carriers, and are formulated using conventional techniques known to those of ordinary skill in the art. In the most preferred embodiment, the ingredients are formulated into cream having a viscosity of 35,000 to 45,000 cps (measured on a Brookfield LVT Viscometer with a T/C spindle at 5 rpm) and a specific gravity of 0.9990 to 1.100.

The term "topical composition" as used herein shall mean the complete product including the S-acyl glutathione active ingredient, the carrier, and any adjuvants, thickeners, excipients, etc. as described herein which is applied to a person's skin.

The quantity of S-acyl glutathione active ingredient in the carrier may be varied or adjusted widely depending upon the particular application, the potency of the particular compound or the desired concentration. Generally, the quantity of S-acyl glutathione active ingredient will range between about 0.01% to about 20% by weight of the topical composition, more preferably, about 0.1% to about 5% by weight. In some applications, the quantity of S-acyl glutathione active ingredient will exceed 5% by weight. Generally, lower concentrations of S-acyl glutathione active ingredients in a carrier are suitable, depending upon the application regimen and the active and adjunct ingredients employed. In the most preferred embodiment, S-palmitoylglutathione is present from about 1.00% to about 3.00% by weight.

Generally in the practice of methods of the invention, the topical composition is topically applied to the skin areas, such as that of the face, at predetermined intervals often as a moisturizer, lotion, or cream, it generally being the case that gradual improvement is noted with each successive application. Although immediate effects can be observed, enhanced results are observed when the topical composition is applied twice daily, preferably in the morning and evening. Insofar as has been determined based upon clinical studies to date, no adverse side effects are encountered. It is an advantage of the invention that compositions of the invention do not require a pharmaceutical prescription.

The topical composition of the invention can contain additional ingredients commonly found in skin care compositions and cosmetics, such as, for example, tinting agents, emollients, skin conditioning agents, emulsifying agents, humectants, preservatives, antioxidants, perfumes, chelating agents, etc., provided that they are physically and chemically compatible with other components of the composition.

Preservatives include, but are not limited to, $C_1$-$C_3$ alkyl parabens and phenoxyenthanol, typically present in an amount ranging from about 0.1% to about 2.0% by weight percent, based on the total composition. A preferred preservative is ISP's Optiphen™ Plus, a liquid preservative formulation featuring a blend of phenoxyethanol, sorbic acid and an emollient base.

Emollients, typically present in amounts ranging from about 0.01% to 10% of the total composition include, but are not limited to, fatty esters, fatty alcohols, mineral oils, polyether siloxane copolymers, docosahexanoic acid (DHA) and mixtures thereof. Preferred emollients are Actiglow® (hydrolyzed glycosaminoglycans, propylene glycol, water, phenoxethanol) by Active Organics, squalane, shae butter, meadowfoam seed oil, isopropyl palmitate and DHA.

Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. A preferred humectant is shae butter.

Emulsifiers, typically present in amounts from about 1% to about 15% by weight of the composition, include, but are not limited to, stearic acid, cetyl alcohol, stearyl alcohol, steareth 2, steareth 20, acrylates/C10-30 alkyl acrylate crosspolymers, silicones, dimethylethanolamine (DMAE), phosphatidylcholine (PPC), docosahexanoic acid (DHA) and mixtures thereof. Preferred emulsifiers are sodium hyaluronate, Promulgen-D® (a mixture of 75% cetostearyl alcohol and 25% ethoxylate cetostearyl alcohol sold by Amerchol Corp.), Arlacel™ 165 (Glyceryl Stearate and PEG-100 Stearate sold by Croda Inc.) silicone (Dow Corning® 200 Fluid, 350 CST), dimethylaminoethanol, also known as DMAE, and Phospholipon® 90 G (phosphatidylcholine with 10% fatty acids sold by Phospholipid GmbH).

Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof.

Antioxidants, typically present in an amount ranging from about 0.01% to about 0.75% by weight of the composition, include, but are not limited to, butylated hydroxy toluene (BHT); vitamin C and/or vitamin C derivatives, such as fatty acid esters of ascorbic acid, particularly ascorbyl palmitate; butylated hydroanisole (BHA); phenyl-α-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. Particularly preferred antioxidants are those that provide additional benefits to the skin such as ascorbyl palmitate, sesame seed oil, alpha-lipoic acid, and Tocomin® 50 (palm oil, tocotrienols, tocopherol).

Buffering agents are employed in many compositions. Preferably, the amount of buffering agent is one that results in compositions having a pH ranging from about 4.0 to about 8.5, more preferably from about 4.5 to about 7.0, most preferably from about 5.0 to about 6.0. Typical buffering agents are chemically and physically stable agents commonly found in cosmetics, and can include compounds that are also adjunct ingredients such as citric acid, malic acid, and glycolic acid buffers.

Some embodiments of this invention contain at least one other adjunct ingredient in addition to S-acyl glutathione. Adjunct ingredients present in an amount ranging from 0.01% to about 20% by weight of the composition include, but are not limited to one or more of: isothiocyanates, caffeine, vitamin D3, lipoic acid; α-hydroxy acids such as glycolic acid or lactic acid; ascorbic acid and its derivatives, especially fatty acid esters of ascorbic acid; or tocotrienols and tocotrienol derivatives and vitamin E compositions enriched with tocotrienols or tocotrienol derivatives; and neuropeptides. Preferred adjunct agents include glycolic acid, citric acid, ascorbyl palmitate, Sepitonic™ M3 by Seppic, which contains magnesium aspartate, zinc gluconate and copper gluconate, Tocomin® 50, and Oligopeptide-17 and Oligopeptide-49.

Additional ingredients and methods as disclosed in my U.S. Pat. Nos. 5,376,361; 5,409,693; 5,545,398; 5,554,647; 5,574,063; 5,643,586; 5,709,868; 5,879,690; 6,191,121; 6,296,861; 6,437,004; and 6,979,459, which are hereby incorporated by reference, may also be used.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES

Formulation: A formulation for an oil in water emulsion prepared by combing the following ingredients using conventional mixing techniques.

| Material | Grade | Wt. % |
| --- | --- | --- |
| Purified Water | USP | 55-65 |
| S-palmitoyl glutathione | Cosmetic | 1.0-3.0 |
| Mineral (magnesium, copper, zinc) salts | Cosmetic | 6-10 |
| Fatty acid derivatives of stearic acid | Cosmetic | 1.5-11 |
| Isopropyl Palmitate | NF | 1.0-5.0 |
| Tetrahexyldecyl ascorbate | NF, FCC | 1.0-5.0 |
| Hydrolyzed glycosaminoglycans | Cosmetic | 0.5-3.5 |
| DMAE | Cosmetic | 0.25-3.5 |
| Phosphatidylcholine | Cosmetic | 1.0-3.0 |
| L-Tyrosine | Cosmetic | 1.0-3.0 |
| Squalane | Cosmetic | 0.5-1.5 |
| Glycolic Acid | Cosmetic | 0.5-1.5 |
| Sesame seed oil/meadowfoam seed oil | Cosmetic | 0.25-1.5 |
| Oligopeptides | Cosmetic | 0.5-3.0 |
| Glycerin | USP | 0.25-0.75 |
| Phenoxyethanol based preservatives | Cosmetic | 0.25-0.75 |
| Dimethicone | Cosmetic | 0.25-0.75 |
| DHA | Cosmetic | 0.25-0.75 |
| Tocotrienols | Cosmetic | 0.125-0.50 |
| Disodium EDTA | Cosmetic | 0.05-0.50 |
| Citric Acid | Cosmetic | 0.05-0.50 |
| Alpha-lipoic Acid | Cosmetic | 0.005-0.150 |
| Ascorbyl Palmitate | Cosmetic | 0.005-0.150 |
| Fragrance | Cosmetic | 0.005-0.50 |

Clinical Study: 43 female subjects, between the ages of 44-56 years and in good health participated in a home-use testing study of the foregoing oil in water formulation (the "Product"). All subjects has self-perceived "marionette" lines, smile lines, deep nasolabial fold lines, crow's feet, fine lines/wrinkles, vertical lines between the eyebrows, horizontal forehead lines, sagging thin/frail skin, skin redness and dullness. Each subject had baseline photographs taken with a Visia CR® Digital Imaging System. Subjects applied the Product at the baseline visit. Immediately after Product application, subjects answered a questionnaire and photographs were repeated. Subjects were given the Product and instructed to return after 4 weeks of product use onto a clean face and neck, morning and evening. At the final 4-week visit, subjects answered a questionnaire and had a final set of photographs taken.

Results: Immediately after the first Product application, subjects reported a 38% to 73% improvement in the appearance lines and wrinkles, look, feel, and appearance of the skin. After 4-weeks of application, subjects reported an 80% to 95% improvement in the appearance of lines and wrinkles, look, feel, and appearance of skin. Specifically improvement was seen for "marionette" lines, "eleven" lines, horizontal forehead lines, "papery" look of skin, roundness and fullness of cheeks, natural radiance, tightness and firmness, smoothness and softness, tone, elasticity and resiliency, moisture and hydration, redness/blotchiness, discoloration, pore size, sagging, and overall youthfulness of skin.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method of improving the appearance of aging skin comprising: applying to skin tissue having dullness or lack of radiance, a safe and effective amount of a composition containing S-acyl glutathione derivative of formula (I);

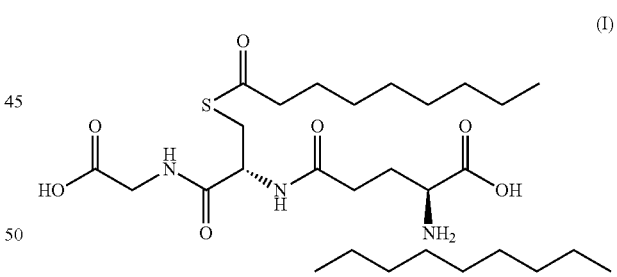

and a dermatologically acceptable carrier;
in a sufficient amount and for a sufficient time to improve the dullness or lack of radiance of the skin tissue.

2. The method of claim 1, wherein the composition comprises about 0.01% to about 20% by weight of S-palmitoyl glutathione derivative.

3. The method of claim 2, wherein the composition comprises about 0.1% to about 5% by weight of S-palmitoyl glutathione derivative.

4. The method of claim 3, wherein the composition comprises about 1.0% to about 3% by weight of S-palmitoyl glutathione.

5. The method of claim 1, wherein the composition further comprises one or more additional ingredients selected from the group consisting of: ascorbic acid, ascorbic acid derivatives, lipoic acid, neuropeptides, α-hydroxy acids, salts of magnesium, zinc and copper, tocotrienols, tocotrienol derivatives and vitamin E compositions enriched with tocotrienols or tocotrienol derivatives.

6. The method of claim 1, wherein the skin tissue also has dryness.

7. The method of claim 1, wherein the skin tissue also has wrinkles and lines.

8. The method of claim 1, wherein the skin tissue also has enlarged pores.

9. The method of claim 1, wherein the skin tissue is peri-menopausal, menopausal, or post-menopausal skin.

10. A method of treating marionette lines to improve the appearance thereof, comprising: applying to human skin tissue having marionette lines a safe and effective amount of a composition containing S-acyl glutathione derivative of formula (I);

(I)

[Chemical structure of formula (I)]

and a dermatologically acceptable carrier;
  in a sufficient amount and for a sufficient time to improve the appearance of the marionette lines.

11. The method of claim 10, wherein the composition comprises about 0.01% to 20% by weight of S-palmitoyl glutathione derivative.

12. The method of claim 11, wherein the composition comprises about 0.1% to 5% by weight of S-palmitoyl glutathione derivative.

13. The method of claim 12, wherein the composition comprises about 1.0% to 3% by weight S-palmitoyl glutathione.

14. The method of claim 10, wherein the composition further comprises one or more additional ingredients selected from the group consisting of: ascorbic acid, ascorbic acid derivatives, lipoic acid, neuropeptides, α-hydroxy acids, salts of magnesium, zinc and copper, tocotrienols, tocotrienol derivatives and vitamin E compositions enriched with tocotrienols or tocotrienol derivatives.

15. The method of claim 10, wherein the skin tissue also has additional lines and wrinkles and the method treats the additional lines and wrinkles.

16. The method of claim 15, wherein the additional lines and wrinkles comprises eleven lines.

17. The method of claim 15, wherein the additional lines and wrinkles comprise horizontal forehead lines.

18. The method of claim 10, wherein the skin tissue also has sagging skin and the method improves the appearance thereof.

19. The method of claim 10, wherein the skin tissue also has dryness and the method improves the appearance thereof.

20. The method of claim 10, wherein the skin tissue also has discoloration and the method improves the appearance thereof.

21. The method of claim 10, wherein the skin tissue also has redness or blotchiness and the method improves the appearance thereof.

22. The method of claim 21, wherein the redness or blotchiness is comprised of spider vessels.

23. The method of claim 10, wherein the skin is peri-menopausal, menopausal, or post-menopausal skin.

24. A method of treating eleven lines to improve the appearance thereof comprising: applying to human skin tissue having eleven lines, a safe and effective amount of a composition containing S-acyl glutathione derivative of formula (I):

(I)

[Chemical structure of formula (I)]

and a dermatologically acceptable carrier;
  in a sufficient amount and for a sufficient time to improve the appearance of the eleven lines.

25. The method of claim 24, wherein the composition comprises about 0.01% to 20% by weight of S-palmitoyl glutathione derivative.

26. The method of claim 25, wherein the composition comprises about 0.1% to 5% by weight of S-palmitoyl glutathione derivative.

27. The method of claim 26, wherein the composition comprises about 1.0% to 3% by weight S-palmitoyl glutathione.

28. The method of claim 24, wherein the skin tissue is peri-menopausal, menopausal, or post-menopausal skin.

29. A method of treating horizontal forehead lines to improve the appearance thereof comprising: applying to human skin tissue having horizontal forehead lines, a safe and effective amount of a composition containing S-acyl glutathione derivative of formula (I):

(I)

[Chemical structure of formula (I)]

and a dermatologically acceptable carrier;
  in a sufficient amount and for a sufficient time to improve the appearance of the horizontal forehead lines.

30. The method of claim 29, wherein the composition comprises about 0.01% to 20% by weight of S-palmitoyl glutathione derivative.

31. The method of claim 30, wherein the composition comprises about 0.1% to 5% by weight of S-palmitoyl glutathione derivative.

32. The method of claim 31, wherein the composition comprises about 1.0% to 3% by weight S-palmitoyl glutathione.

33. The method of claim 29, wherein the skin tissue is peri-menopausal, menopausal, or post-menopausal skin.

34. A method of treating sagging skin to improve the appearance thereof comprising: applying to human skin tissue having sagging skin, a safe and effective amount of a composition containing S-acyl glutathione derivative of formula (I):

[Chemical structure of formula (I)]

and a dermatologically acceptable carrier;
in a sufficient amount and for a sufficient time to improve the appearance of the sagging skin.

35. The method of claim 34, wherein the composition comprises about 0.01% to 20% by weight of S-palmitoyl glutathione derivative.

36. The method of claim 35, wherein the composition comprises about 0.1% to 5% by weight of S-palmitoyl glutathione derivative.

37. The method of claim 36, wherein the composition comprises about 1.0% to 3% by weight S-palmitoyl glutathione.

38. The method of claim 34, wherein the skin tissue is peri-menopausal, menopausal, or post-menopausal skin.

39. A method of treating spider vessels in red or blotchy skin to improve the appearance thereof comprising: applying to human skin tissue having spider vessels in red or blotchy skin, a safe and effective amount of a composition containing S-acyl glutathione derivative of formula (I):

[Chemical structure of formula (I)]

and a dermatologically acceptable carrier;
in a sufficient amount and for a sufficient time to improve the appearance of the spider vessels in red or blotchy skin.

40. The method of claim 39, wherein the composition comprises about 0.01% to 20% by weight of S-palmitoyl glutathione derivative.

41. The method of claim 40, wherein the composition comprises about 0.1% to 5% by weight of S-palmitoyl glutathione derivative.

42. The method of claim 41, wherein the composition comprises about 1.0% to 3% by weight S-palmitoyl glutathione.

43. The method of claim 39, wherein the skin tissue is peri-menopausal, menopausal, or post-menopausal skin.

44. A method of treating enlarged pores to improve the appearance thereof comprising: applying to human skin tissue having enlarged pores, a safe and effective amount of a composition containing S-acyl glutathione derivative of formula (I):

[Chemical structure of formula (I)]

and a dermatologically acceptable carrier
in a sufficient amount and for a sufficient time to improve the appearance of the enlarged pores.

45. The method of claim 44, wherein the composition comprises about 0.01% to 20% by weight of S-palmitoyl glutathione derivative.

46. The method of claim 45, wherein the composition comprises about 0.1% to 5% by weight of S-palmitoyl glutathione derivative.

47. The method of claim 46, wherein the composition comprises about 1.0% to 3% by weight S-palmitoyl glutathione.

48. The method of claim 44, wherein the skin tissue is peri-menopausal, menopausal, or post-menopausal skin.

49. A method of treating skin which is dull and lacking radiance to improve the appearance thereof comprising: applying to human skin tissue which is dull and lacking radiance, a safe and effective amount of a composition containing S-acyl glutathione derivative of formula (I):

[Chemical structure of formula (I)]

and a dermatologically acceptable carrier
in a sufficient amount and for a sufficient time to improve the appearance of the skin which is dull and lacking in radiance.

50. The method of claim 49, wherein the composition comprises about 0.01% to 20% by weight of S-palmitoyl glutathione derivative.

51. The method of claim 50, wherein the composition comprises about 0.1% to 5% by weight of S-palmitoyl glutathione derivative.

52. The method of claim 51, wherein the composition comprises about 1.0% to 3% by weight S-palmitoyl glutathione.

53. The method of claim 49, wherein the skin tissue is peri-menopausal, menopausal, or post-menopausal skin.

54. A method of improving the appearance of aging skin comprising: applying to skin tissue having enlarged pores, a safe and effective amount of a composition containing S-acyl glutathione derivative of formula (I)

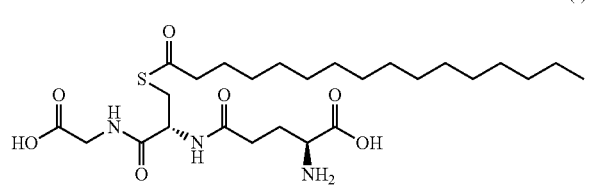

(I)

and a dermatologically acceptable carrier;

in a sufficient amount and for a sufficient time to improve the appearance of the enlarged pores.

55. The method of claim 54, wherein the composition comprises about 0.01% to 20% by weight of S-palmitoyl glutathione derivative.

56. The method of claim 55, wherein the composition comprises about 0.1% to 5% by weight of S-palmitoyl glutathione derivative.

57. The method of claim 56, wherein the composition comprises about 1.0% to 3% by weight S-palmitoyl glutathione.

58. The method of claim 54, wherein the skin tissue is peri-menopausal, menopausal, or post-menopausal skin.

59. A method of improving the appearance of aging skin comprising: applying to skin tissue having marionette lines, a safe and effective amount of a composition containing S-acyl glutathione derivative of formula (I)

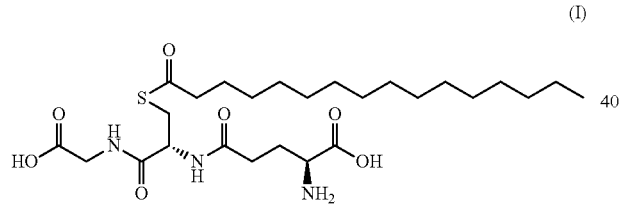

(I)

and a dermatologically acceptable carrier;

in a sufficient amount and for a sufficient time to improve the appearance of the marionette lines.

60. The method of claim 59, wherein the composition comprises about 0.01% to 20% by weight of S-palmitoyl glutathione derivative.

61. The method of claim 60, wherein the composition comprises about 0.1% to 5% by weight of S-palmitoyl glutathione derivative.

62. The method of claim 61, wherein the composition comprises about 1.0% to 3% by weight S-palmitoyl glutathione.

63. The method of claim 59, wherein the skin tissue is peri-menopausal, menopausal, or post-menopausal skin.

64. A method of improving the appearance of aging skin comprising: applying to skin tissue having eleven lines, a safe and effective amount of a composition containing S-acyl glutathione derivative of formula (I)

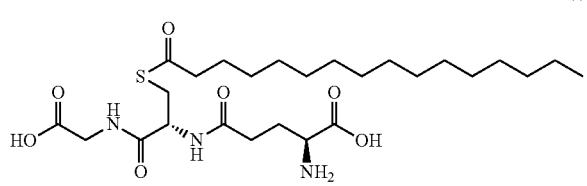

(I)

and a dermatologically acceptable carrier;

in a sufficient amount and for a sufficient time to improve the appearance of the eleven lines.

65. The method of claim 64, wherein the composition comprises about 0.01% to 20% by weight of S-palmitoyl glutathione derivative.

66. The method of claim 65, wherein the composition comprises about 0.1% to 5% by weight of S-palmitoyl glutathione derivative.

67. The method of claim 66, wherein the composition comprises about 1.0% to 3% by weight S-palmitoyl glutathione.

68. The method of claim 64, wherein the skin tissue is peri-menopausal, menopausal, or post-menopausal skin.

69. A method of improving the appearance of aging skin comprising: applying to skin tissue having horizontal forehead lines, a safe and effective amount of a composition containing S-acyl glutathione derivative of formula (I)

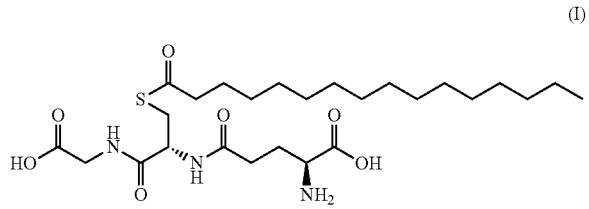 [SMILES: CCCCCCCCCCCCCCCC(=O)SC[C@H](NC(=O)CC[C@H](N)C(=O)O)C(=O)NCC(=O)O]

(I)

and a dermatologically acceptable carrier;

in a sufficient amount and for a sufficient time to improve the appearance of the horizontal forehead lines.

70. The method of claim 69, wherein the composition comprises about 0.01% to 20% by weight of S-palmitoyl glutathione derivative.

71. The method of claim 70, wherein the composition comprises about 0.1% to 5% by weight of S-palmitoyl glutathione derivative.

72. The method of claim 71, wherein the composition comprises about 1.0% to 3% by weight S-palmitoyl glutathione.

73. The method of claim 69, wherein the skin tissue is peri-menopausal, menopausal, or post-menopausal skin.

74. A method of improving the appearance of aging skin comprising: applying to skin tissue having sagging skin, a safe and effective amount of a composition containing S-acyl glutathione derivative of formula (I)

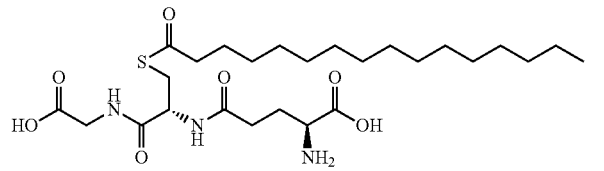 (I)

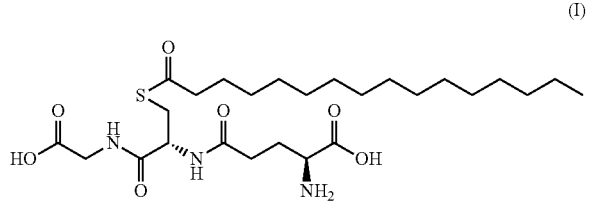 [SMILES: CCCCCCCCCCCCCCCC(=O)SC[C@H](NC(=O)CC[C@H](N)C(=O)O)C(=O)NCC(=O)O] (I)

and a dermatologically acceptable carrier;
in a sufficient amount and for a sufficient time to improve the appearance of the sagging skin.

75. The method of claim 74, wherein the composition comprises about 0.01% to 20% by weight of S-palmitoyl glutathione derivative.

76. The method of claim 75, wherein the composition comprises about 0.1% to 5% by weight of S-palmitoyl glutathione derivative.

77. The method of claim 76, wherein the composition comprises about 1.0% to 3% by weight S-palmitoyl glutathione.

78. The method of claim 74, wherein the skin tissue is peri-menopausal, menopausal, or post-menopausal skin.

79. A method of improving the appearance of aging skin comprising: applying to skin tissue having spider vessels in red or blotchy skin, a safe and effective amount of a composition containing S-acyl glutathione derivative of formula (I) and a dermatologically acceptable carrier;
in a sufficient amount and for a sufficient time to improve the appearance of the spider vessels in the red or blotchy skin.

80. The method of claim 79, wherein the composition comprises about 0.01% to 20% by weight of S-palmitoyl glutathione derivative.

81. The method of claim 80, wherein the composition comprises about 0.1% to 5% by weight of S-palmitoyl glutathione derivative.

82. The method of claim 81, wherein the composition comprises about 1.0% to 3% by weight S-palmitoyl glutathione.

83. The method of claim 79, wherein the skin tissue is peri-menopausal, menopausal, or post-menopausal skin.

\* \* \* \* \*